United States Patent [19]
Theron

[11] Patent Number: 5,423,742
[45] Date of Patent: Jun. 13, 1995

[54] METHOD FOR THE WIDENING OF STRICTURES IN VESSELS CARRYING BODY FLUID

[75] Inventor: Jacques Theron, Fleury sur One, France

[73] Assignee: Schneider Europe, Zurich, Switzerland

[21] Appl. No.: 137,398

[22] Filed: Oct. 14, 1993

Related U.S. Application Data

[63] Continuation of Ser. No. 933,620, Aug. 21, 1992, abandoned, which is a continuation of Ser. No. 728,859, Jul. 11, 1991, abandoned, which is a continuation of Ser. No. 457,216, Dec. 26, 1989, abandoned.

[30] Foreign Application Priority Data

Sep. 12, 1989 [DE] Germany ............... 8910856 U

[51] Int. Cl.⁶ .................................. A61M 29/02
[52] U.S. Cl. ............................. 604/28; 604/101; 604/53; 606/194
[58] Field of Search ............... 606/194, 192, 159; 604/96, 101, 28, 53

[56] References Cited

U.S. PATENT DOCUMENTS

| | | | |
|---|---|---|---|
| 4,299,226 | 11/1981 | Banka | 604/97 X |
| 4,610,662 | 9/1986 | Weikl et al. | 604/101 X |
| 4,655,746 | 4/1987 | Daniels et al. | 604/101 X |
| 4,762,129 | 8/1988 | Bonzel | 604/96 X |
| 4,794,928 | 1/1989 | Kletschka | 604/101 X |
| 4,798,586 | 1/1989 | Stevens | 606/194 X |
| 4,846,174 | 7/1989 | Willard et al. | 604/96 X |
| 4,911,163 | 3/1990 | Fina | 606/192 X |
| 5,102,390 | 4/1992 | Crittenden et al. | 604/101 X |

Primary Examiner—Michael H. Thaler
Attorney, Agent, or Firm—Peter C. Richardson; Lawrence C. Akers; John L. LaPierre

[57] ABSTRACT

A catheter device having, in coaxial arrangement, an insertion catheter, a dilation catheter and an occlusion catheter. By means of the occlusion catheter a vessel carrying body fluid is closed off in the direction of flow following a stricture. By means of the dilation catheter, the stricture is treated by dilation. The occlusion catheter positioned beyond the stricture prevents an embolism due to detached particles flowing off. After treatment of the stenosis, vessel fluid together with any detached particles is removed by suction and washed out through the insertion catheter.

8 Claims, 3 Drawing Sheets

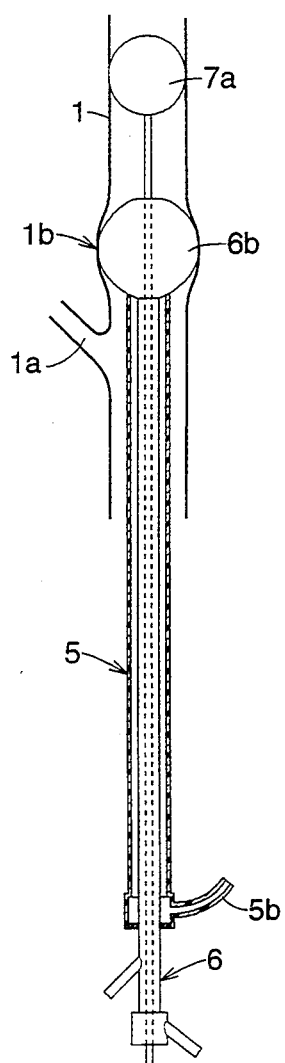
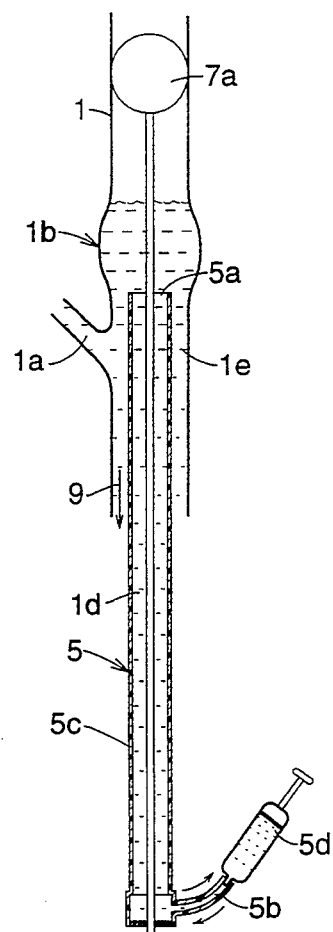
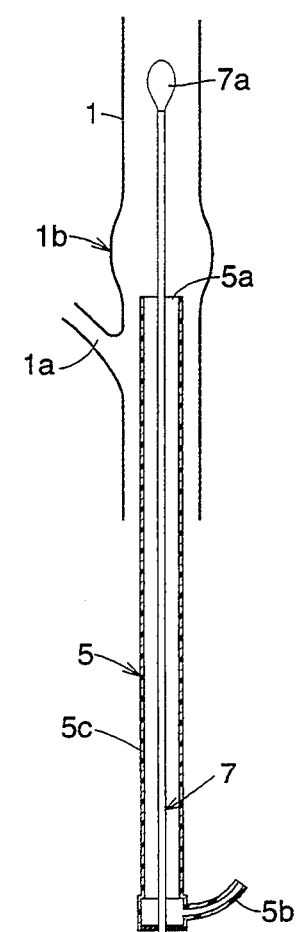
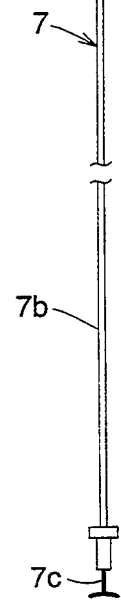
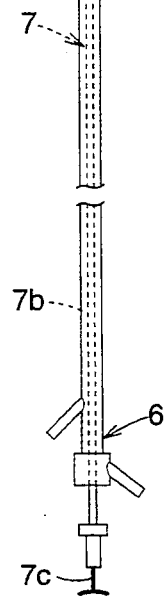
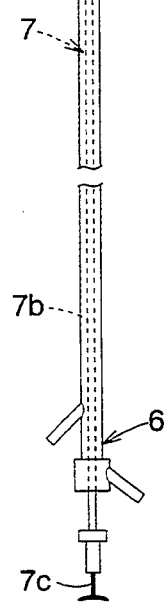
FIG. 3D  FIG. 3E  FIG. 3F

METHOD FOR THE WIDENING OF STRICTURES IN VESSELS CARRYING BODY FLUID

This is a continuation of application Ser. No. 07/933,620, filed on Aug. 21, 1992 now abandoned, which is a continuation of application Ser. No. 07/728,859, filed on Jul. 11, 1991, now abandoned, which is a continuation of application Ser. No. 07/457,216 filed on Dec. 26, 1989, now abandoned.

BACKGROUND OF THE INVENTION

This invention relates to dilation catheters in general, and in particular to a catheter device having an insertion catheter, dilation catheter and occlusion catheter in coaxial arrangement.

Percutaneous transluminal angioplasty of arteriosclerotic deposits or atheroma in the carotid artery was hitherto regarded as involving risks, since vessel parts detached during dilation might cause a cerebral embolism. In order to reduce the risk of embolism, a catheter device is known in the art which has, in addition to the dilation catheter, a so-called occlusion catheter with which the vessel is for a short time closed downstream. Treatment with this prior art catheter device is awkward, especially since in this case two separate entry points are necessary for the two catheters. Thus, in order to reach the stenosis, two accesses are required in the inguinal region of the patient.

A primary object of the present invention is, therefore, to provide a catheter device including an occlusion component which puts less strain on the patient and is easier to handle, and which nevertheless effectively inhibits the occurrence of a cerebral embolism. Another object of the present invention is to provide such a catheter device which provides in coaxial arrangement an insertion catheter, dilation catheter and occlusion catheter which are sealed off with respect to each other and which are individually displaceable in the longitudinal direction. These and other objects will be apparent throughout the description which follows.

SUMMARY OF THE INVENTION

The present invention is a catheter device comprising an insertion catheter, dilation catheter and occlusion catheter which are sealed off with respect to each other, are arranged coaxially to each other, and are introduced into the blood vessel to be treated through the same entry opening. The catheters are displaceable relative to each other in the longitudinal direction so that, for example, the dilation catheter can be brought into a retracted position.

In a preferred embodiment, the insertion catheter has at the distal end an opening which can be in communication with a syringe and through which any vessel particles which have become detached during treatment can be removed by suction or washed out. The removal by suction and washing-out is preferably carried out with the dilation catheter retracted and the occlusion catheter inserted. The occlusion catheter has preferably at its distal end a dilatable latex balloon with which the vessel to be treated can be closed off in the direction of flow following the stenosis.

BRIEF DESCRIPTION OF THE DRAWINGS

An exemplary embodiment of the invention is described in greater detail below with reference to the drawings in which:

FIG. 3a–3f show, in order to illustrate the function of the catheter device, schematic representations of a vessel section and the catheter device.

DETAILED DESCRIPTION OF A PREFERRED EMBODIMENT

Figure 1:
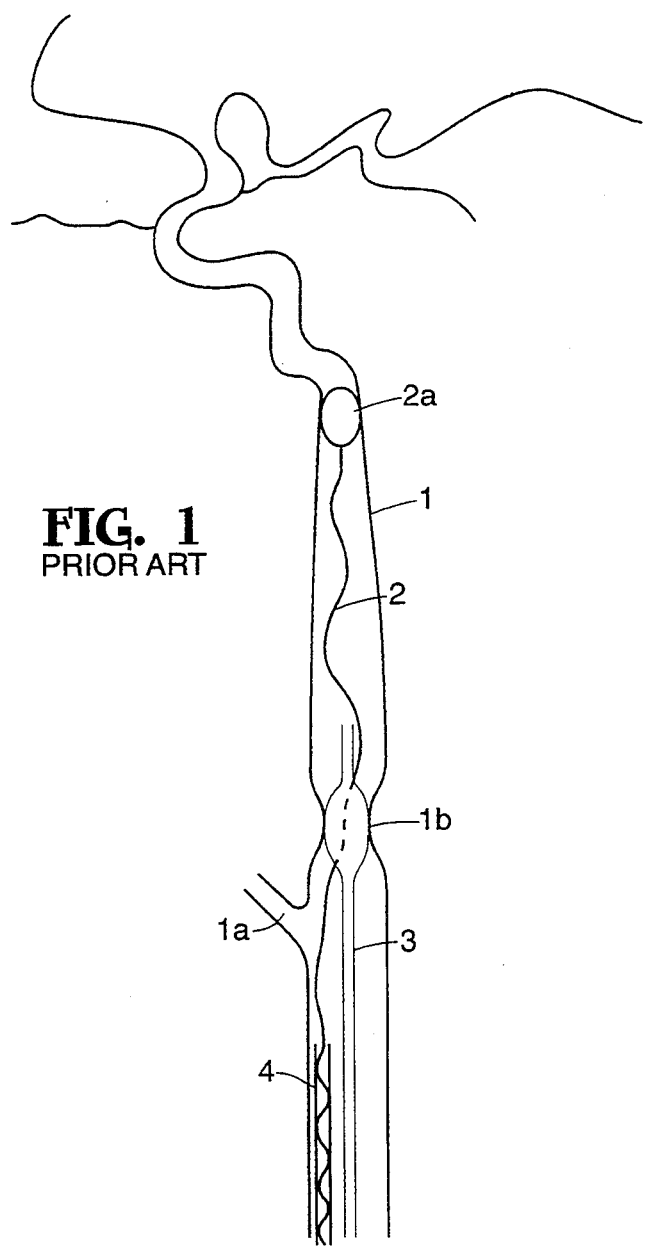
FIG. 1 shows a schematic representation of a vessel section with an inserted catheter device according to the prior art.

FIG. 1 shows a blood vessel 1 which, downstream from a lateral branch 1a, is partially closed by a stenosis 1b. The known prior-art catheter device shown here has an occlusion catheter 2 having a balloon 2a which can be introduced into the vessel 1 through an insertion catheter 4. Parallel to the insertion catheter 4 and the occlusion catheter 2, a dilation catheter 3 is introduced into the vessel 1 in order to dilate the stenosis. The proximal ends of the dilation catheter 3 and the insertion catheter 4 lead outwards through separate entry points in the inguinal region of the patient.

Figure 2:
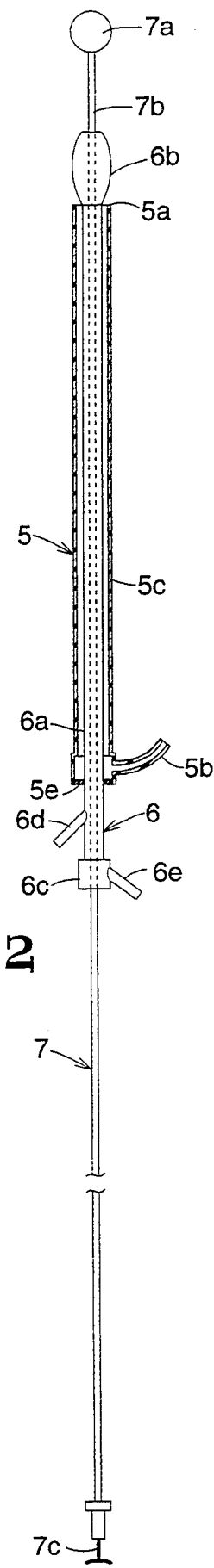
FIG. 2 shows a longitudinal section through a catheter device of the present invention.

The catheter device of the present invention shown in FIG. 2 has a guide catheter 5 with a flexible catheter tube 5c which has an internal diameter of at least 2 mm. At the proximal end of the catheter tube 5c a connection 5b is arranged for a syringe 5d as shown in FIG. 3e. At the distal end the catheter tube 5c has an opening 5a through which vessel fluid, with any detached particles, can be removed by suction from the area of the stenosis 1b by means of the syringe 5d.

The insertion catheter 5 is passed through, in coaxial arrangement, by a dilation catheter 6 having a catheter tube 6a which has a lumen (not shown) and, at the proximal end, a syringe connection for dilating a balloon 6b. The external diameter of the catheter tube 6a is substantially smaller than the internal diameter of the insertion catheter 5c, so that between these two catheters 5 and 6 there is a passage for the fluid drawn off or injected at the inlet opening 5a.

The dilation catheter 6 is likewise in turn passed through, in coaxial arrangement, by an occlusion catheter 7. The latter has, at the distal end of a flexible catheter tube 7b, a latex balloon 7a which is connected to a syringe 7c and is filled with an isotonic saline solution as the inflating medium. The catheter tube 7b is preferably of polytetrafluoroethylene and is continuously hollow inside so that there is a connection between the inside of the balloon 7a and the pump 7c. The occlusion catheter 7 has, for example, a length of 250 to 300 cm and at the same time forms a guide for the dilation catheter 6 displaceable upon it. The balloon 7a is a comparatively soft and elastic latex balloon, whereas the dilation balloon 6b in the inflated state has an exactly defined external diameter.

At the proximal end of the insertion catheter 5 a seal 5e is arranged, by means of which seal this catheter is sealed off with respect to the dilation catheter 6 in a fluid-tight and displaceable manner. A similar seal 6c is arranged at the proximal end of the balloon catheter 6. Seals of this type are known per se. Also known are connections 6d and 6e on the dilation catheter 6, which are connected to lumina (not shown here) of the dilation catheter. Dilation catheters of this type are likewise well known per se.

Figure 3A:
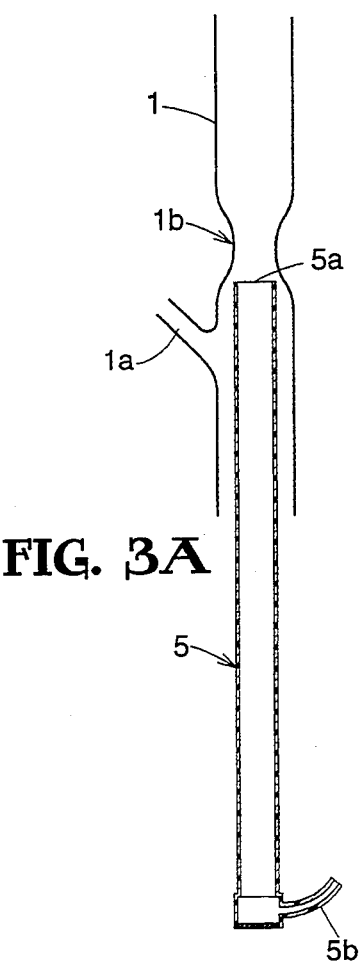
Figure 3B:
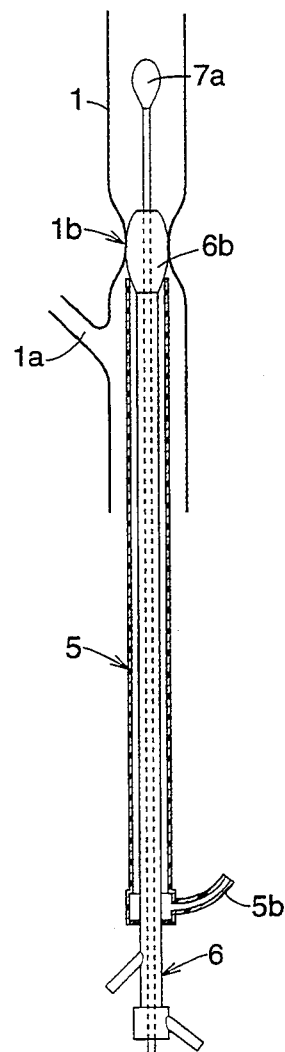
Figure 3C:
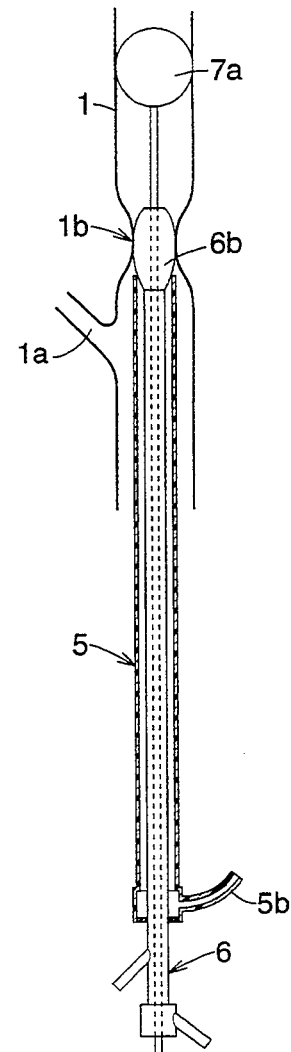

The individual steps for treating a stenosis 1b in a vessel 1, and in particular in a carotid artery, are illustrated below with references to FIGS. 3a–3f. The insertion catheter 5 is pushed through an opening in the inguinal region of the patient into the vessel 1, until its front opening 5a is situated, as shown in FIG. 3a, directly in front of the stenosis 1b. If appropriate, an exchange catheter (not shown here and known per se) is used in this respect. The proximal end of the insertion catheter 5 is, or course, closed in this respect. The occlusion catheter 7 is now inserted into the guide catheter 5 positioned in this way and is placed distal of the stenosis, and the balloon is stabilized in the inflated state. The dilation catheter 6 is then pushed over the occlusion catheter 7, and the balloon 6b is placed in the middle of the stenosis. Anticoagulants are then injected through the central lumen of the dilation catheter.

For the actual treatment of the stenosis 1b, the dilation balloon 6b is now dilated in a known manner. Before dilation, atropine can also be injected through the dilation catheter 6 in order to slow the action of the heart. After treatment of the stenosis 1b the dilation balloon 6b is emptied and the dilation catheter 6 is retracted, as shown in FIG. 3e. With the occlusion catheter 7 simultaneously inflated, vessel fluid 1e and any detached particles 1d present are removed by suction through the insertion catheter 5 by means of the syringe 5d. Since the dilation catheter 6 is retracted in front of the seal 5e, a comparatively wide passage is now available between the catheters 5 and 7. As a result of pressure exerted by means of the syringe 5d, vessel fluid with small detached parts can be rinsed off through this passage in the direction of the arrow 9. The parts thus reach areas of the vessel where there is no danger of embolism. Finally, the balloon 7a is now also returned to the emptied state and the catheter device is removed from the vessel 1.

What is claimed is:

1. A method for widening a stricture in a body vessel carrying a body fluid comprising the steps of:
   a) providing a catheter device comprising an outermost insertion catheter, a central dilation catheter having a central lumen and being disposed within the insertion catheter and having a first balloon being inelastic and adapted for expansion to a precise predetermined external diameter upon inflation to dilate a stenosis in the body vessel, and an innermost combination dilation-catheter guide and occlusion catheter disposed within the dilation catheter having a proximal end which extends proximally from the dilation catheter and a distal end with a second balloon being elastic and connected to the distal end and adapted for expansion to occlude the body vessel at a location distal of the stenosis, all said catheters being disposed coaxially, all said catheters being longitudinally individually displaceable with respect to each other and all said catheters being sealed fluid tight with respect to each other by a first seal sealing the insertion catheter from the dilation catheter and a second seal sealing the dilation catheter from the occlusion catheter, with said insertion catheter having a distal opening in communication with a proximal connecting piece situated distally from said first seal and adapted to be connected to a pressure and suction device, and further with said dilation catheter, in operative condition, being adapted for independent withdrawal proximally upon said combination dilation-catheter guide and occlusion catheter to a site proximal of said first seal without changing the positioning of said dilation-catheter guide and occlusion catheter;
   b) inserting said catheter device into the body vessel of a patient and advancing the insertion catheter to a site proximally of the stenosis;
   c) advancing the combination dilation-catheter guide and occlusion catheter to a position distally of the stenosis;
   d) inflating said second balloon;
   e) advancing the dilation catheter over the combination dilation-occlusion catheter to a position placing said first balloon centrally of the stenosis; and
   f) inflating said first balloon to dilate said stenosis.

2. The method according to claim 1 wherein after step e) there is further included the step of injecting anticoagulants through the central lumen of the dilation catheter.

3. The method according to claim 1 wherein after step e) there is further included the step of injecting atropine through the central lumen of the dilation catheter.

4. The method according to claim 1 wherein after step f) there is further added step g) of deflating the first balloon and retracting the dilation catheter proximally of said first seal.

5. The method according to claim 4 wherein after step g) there is further added step h) of attaching said pressure and suction device and applying suction to remove any particles detached during stricture widening.

6. The method according to claim 5 wherein step h) comprises applying pressure to wash out and remove any particles detached during stricture widening.

7. The method according to claim 6 wherein after step h) there is further added step i) of deflating said second balloon and removing said catheter device from the body vessel of the patient.

8. The method according to claim 4 followed by the step of deflating said second balloon and removing said catheter device from the body vessel of the patient.

* * * * *